United States Patent
Bunn et al.

(10) Patent No.: US 11,875,339 B1
(45) Date of Patent: Jan. 16, 2024

(54) METHOD AND APPARATUS FOR COLLECTING AND DISTRIBUTING SECURED DATA

(71) Applicant: Meddamark, Inc., Highlands Ranch, CO (US)

(72) Inventors: Robert Bunn, Highlands Ranch, CO (US); Alexander Sheppert, Vineyard, UT (US)

(73) Assignee: Meddamark, Inc., Highlands Ranch, CO (US)

( * ) Notice: Subject to any disclaimer, the term of this patent is extended or adjusted under 35 U.S.C. 154(b) by 0 days.

(21) Appl. No.: 17/991,118

(22) Filed: Nov. 21, 2022

(51) Int. Cl.
  *G06Q 20/36* (2012.01)
(52) U.S. Cl.
  CPC ..... *G06Q 20/3672* (2013.01); *G06Q 2220/00* (2013.01)
(58) Field of Classification Search
  None
  See application file for complete search history.

(56) References Cited

U.S. PATENT DOCUMENTS

| | | | | |
|---|---|---|---|---|
| 10,885,170 | B1* | 1/2021 | Maliani | H04L 9/0643 |
| 11,443,838 | B1* | 9/2022 | Cordonnier | G16H 40/20 |
| 2020/0005284 | A1* | 1/2020 | Vijayan | H04L 63/08 |
| 2021/0133713 | A1* | 5/2021 | Wang | H04L 9/3239 |
| 2022/0351186 | A1* | 11/2022 | Quigley | H04L 9/50 |
| 2022/0383282 | A1* | 12/2022 | Apollo | G06Q 20/065 |
| 2022/0384027 | A1* | 12/2022 | Kaleal, III | G16H 20/40 |
| 2023/0069258 | A1* | 3/2023 | Duarte | G06F 21/602 |

* cited by examiner

*Primary Examiner* — Steven S Kim
*Assistant Examiner* — Jason B Fenstermacher
(74) *Attorney, Agent, or Firm* — Rimon PC; Marc S. Kaufman

(57) ABSTRACT

A decentralized hybrid system for collecting, storing, and managing sensitive data, such as medical record data. Data is stored as multiple atomic records in a centralized database. A non-fungible token (NFT) is associated with each data record and assigned to a cryptographic wallet of a party owning the data in the data record on a blockchain ledger. A user key based on the wallet is stored in a centralized user database to identify the data owner to the system. Ownership tokens are granted for each data record and distributed to parties have an ownership interest in proceeds from the sale of data. When data is purchased, the proceeds are distributed, pro rata, based on the ownership tokens.

9 Claims, 3 Drawing Sheets

METHOD AND APPARATUS FOR COLLECTING AND DISTRIBUTING SECURED DATA

BACKGROUND

Research, for example medical research, often requires a high number of datasets that are relevant to the research being conducted. For example, a medical research facility studying the relationship between existence of a Patent Foraman Ovale (PFO) (an opening between the atria of the heart that exists in roughly 25% of the population) and the occurrence of stroke might want various medical records of stroke victims and persons known to have a PFO. The medical records could include blood test results, imaging studies (such as MRI and ultrasound studies) and other data. Further, it may be desirable to limit or segregate the data by age, race, gender, blood type, lifestyle characteristics, or the like. Medical research and progress is often hindered by a lack of available, relevant, clean, and aggregated data.

Further, medical research relies on other technologies, such as artificial intelligence (AI). As evidenced by the record-setting development of the COVID-19 vaccine, machine-learning and artificial intelligence is a technological field that promises to increase the quality of medical research and thus medical care. The critical requirement of any artificial intelligence project is relevant data. More data allows more training, more iterations, more testing, more correlations, and more scenarios that the AI model can learn from. An AI model is only as powerful as the size and organization of the database used to train the AI model.

Through an archaic process that may have been more relevant when it was created forty years ago, medical databases are condensed via ICD codes to save space. Much of medical data isn't available in digital form. Upon request hospitals are required to furnish medical history data to patients and their designees, but struggle to do so effectively. Often, it can take weeks, just to assemble the medical records of a single patient. Further, the records often consist of scanned, handwritten notes devoid of any universal format. Even when an AI researcher can obtain a sizable medical database, the data's formatting and haphazard organization often prevents effective use of the data for training and AI model or for other purposes.

In the U.S. medical data is legally protected by the Health Insurance Portability and Accountability Act of 1996 (HIPAA). HIPAA is a federal law that required the creation of national standards to protect sensitive patient health information from being disclosed without the patient's consent or knowledge. HIPAA prevents medical information from being disclosed by providers, without express authorization from the individual patients. This further complicates the process of aggregating medical data into a database for Machine-Learning or other research purposes. While HIPAA is a protection for many, the security layers that it has added make it difficult for people to access their own medical data. Further patients that see different doctors can have a hard time transferring their own information from the custody of one doctor to another.

Patients that get lab results or x-rays often have difficulty viewing them. Data is password-protected, hidden behind sign-ups and dual-authentication mechanisms. Different hospitals use different electronic health record systems, and there is little overlap in user experience. Despite the security measures, estimates suggest that 314,063,186 medical records have been hacked since 2009 (up to 94 percent of the USA population). Subjecting the population and medical system to unwieldy security measures has proved largely ineffective in preventing data leaks. Finally, while people legally are in charge of their own medical data, if their data is anonymized and sold, they rarely see any monetary compensation for their data.

SUMMARY OF THE INVENTION

The disclosed implementations allow individuals to share their medical data, and other secured data, in a secured manner. The data is collected, stored in an encrypted from in a centralized database, and secured by a distributed ledger platform, such as a blockchain ledger. The data is clustered (i.e., organized) into datasets that can then be sold to medical researchers and other parties to advance the standards of medical care worldwide. Such parties are often willing to pay a premium for well-organized medical data and proceeds can be distributed to the platform operator, the owners of the data (such as patients), and other relevant parties via a transparent smart-contract on the distributed ledger. All data can be maintained in an anonymous fashion that is HIPAA compliant by anonymizing and aggregating the data statistics. The data can be encrypted and secured with SHA-256 blockchain mechanisms.

A first aspect of the invention is a method and system for securely collecting and storing data, the method comprising: sending a request for data relating to an individual person to a data source, the data being owned by the individual person and the request including a legal release of the data executed by the individual person; in response to the request, receiving the data relating to the individual person from the data source; storing the data relating to an individual person as a data record in a first centralized database, the first centralized database containing other data records that correspond to other data relating to individual persons; creating, by a smart contract on a distributed ledger system, a cryptographic non-fungible token (NFT) based on the data record; assigning the NFT to a cryptographic wallet associated with the individual person on the distributed ledger system; storing a key derived from the cryptographic wallet associated with the individual person in a second centralized database; generating, by a smart contract on a distributed ledger system, at least one ownership token corresponding to the data record; and assigning a portion of the at least one ownership token to the cryptographic wallet associated with the individual person on the distributed ledger system.

A second aspect of the invention is a method for distributing secured data from a database, wherein data relating to an individual person is stored as a data record in a first centralized database, the first centralized database containing other data records that correspond to other data relating to individual persons, and wherein for each data record; (1) a cryptographic non-fungible token (NFT) based on each data record has been created by a smart contract on a distributed ledger and each of the assigned to a respective cryptographic wallet associated with the corresponding individual person on the distributed ledger system, (2) a key derived from each of the cryptographic wallets is associated with the corresponding individual person in a second centralized database and a smart contract on the distributed ledger system has generated at least one ownership token corresponding to respective ones of each of the data records and (3) a portion of the at least one ownership token is assigned to the cryptographic wallet associated with the individual person on the distributed ledger system, the method comprising: receiving a search query from a party requesting data; retrieving relevant data from the first centralized data base that satisfies the query; sending the relevant data to the party requesting the data; receiving payment from the party requesting data; distributing a portion of the payment to each individual person whose data is included in the relevant data in accordance with ownership tokens associated with the data.

BRIEF DESCRIPTION OF THE DRAWINGS

The foregoing summary, as well as the following detailed description of the invention, will be better understood when read in conjunction with the appended drawings. For the purpose of illustrating the invention, there are shown in the appended drawings various illustrative embodiments. It should be understood, however, that the invention is not limited to the precise arrangements and instrumentalities shown. In the drawings.

DETAILED DESCRIPTION

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

Figure 1:
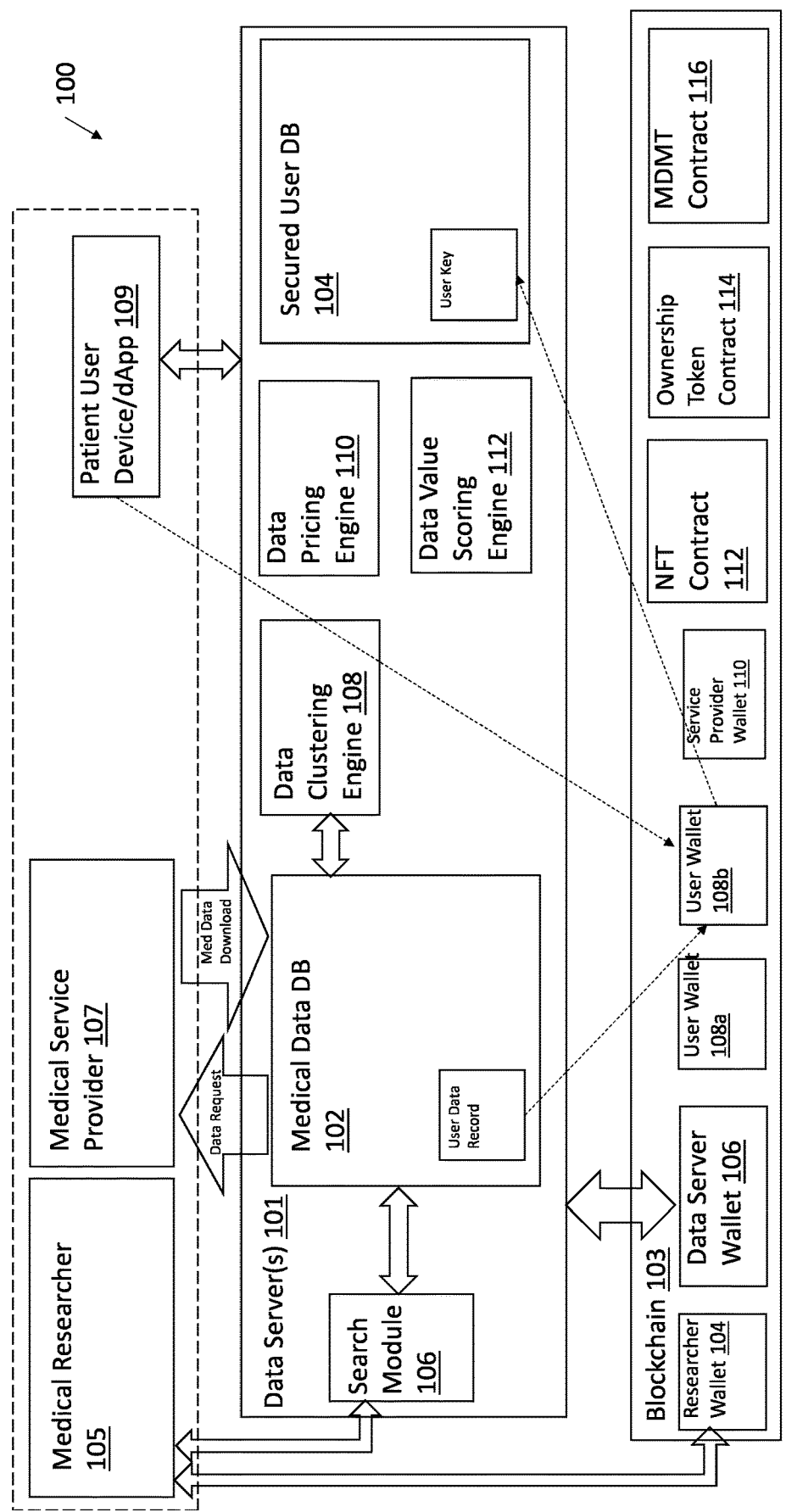
FIG. 1 is a block diagram of a medical data collection and distribution platform in accordance with disclosed implementations.

FIG. 1 illustrates an architecture of a computing system in accordance with disclosed implementations. System 100 can collect and distribute sensitive information, medical information in this example, in a flexible and secure manner while compensating all parties based on data ownership and/or participation in data collection or distribution. System 100 is a hybrid distributed/decentralized computing system with three primary components. The first component is made up of the users of the system, which can include medical researcher/institution computing system 105, medical service provider computing system 107, and patient user devices 109. It will become apparent that there can be any number of users, institutions and service providers, and that various other parties may wish to participate in the system. The second component is data server(s) 101 which provide data collection, storage, processing and distribution services as described in detail below. The third component is a distributed ledger platform, such as blockchain 103 in this example, which, among other things, provides security in the data, tracks ownership, and determines payments, also as described in detail below.

Users wishing to contribute medical data and make money from their data will sign up for an account with server(s) 101 through a user interface, such as a web page presented by server(s) 101 on user device 109, in a known manner. Through the user interface, users can input a list of hospitals, and/or other medical service providers (such as physicians, clinics, labs and the like) that they have visited. Users can also input their personal information, prove their identity in various known manners, and sign a document (i.e., a release such as a standard HIPAA Data Release) that allows a party associated with Data Server(s) 101 (referred to as "data manager" below) to collect their data records from service providers (those listed and possibly future service providers). The data manager will proceed to submit the necessary requests and papers to different medical service providers that will legally require the service providers to send the users' medical data to the data manager.

Once the data manager has received the data, the data can be homogenized and cleaned by data clustering engine 108 to comply with a universal medical record format and data structure schema. The schema can include database classes that contain organized and dated mapping to all of the users' provider notes, scans, diagnoses, and related medical data. These databases can be hosted by the data manager in medical data database 102, and encrypted such that only parties with the correct multi-signature SHA-256 keys will be able to access the data.

The data can be stored in medical data database 102 as data records corresponding to users (patients) and/or as records corresponding to various types of data. The data can be segregated by data clustering engine 108 in various manners to suit the needs of data requestors. After the data is homogenized and secured, data pricing engine 110 will algorithmically create an estimate of the aggregated data's comparative worth to other medical records. The data will be given a value score based on the quality of the data and the amount of data a person has. For example, if a user has contributed data from four MRIs their data will receive a higher value score than somebody who has only had one x-ray imaging procedure. The score can be a dollar value or based on any tool to measure expected value of one set of data compared to another.

A simple algorithm that can be used by data pricing engine is to assign a score to each type data. For example, the scoring below can be used:

MRI of head and neck without contrast: 10
MRI of head and neck with contrast: 20
CAT Scan of head and neck: 5
X-ray image of head and neck: 1

Applying this system to a record of data corresponding to Patient A who has had a MRI of the head and neck without contrast (10 points) and a CAT scan of the head and neck (5 points) would result in a score of 15 for that record. Similarly, if Patient B had an MRI of the head and neck without contrast (10 points) and an MRI of the head and neck with Contrast (20 points) the result of the record for patient B would be 30 points. Such scores can be leveraged in the manner described below.

Distributed ledger technology, such as blockchain 103 in FIG. 1, can be leveraged in a novel manner to provide security accounting and other pragmatic advantages to the system 100. Blockchain technology is extremely secure. For example, the SHA-256 function (the math encrypting and securing the Ethereum Network and many other popular blockchains) has been running for years without ever being hacked. Further blockchain 103 allows public (the full public or a selected participating "public" which is a subset of the full public) transparency into monetary systems without comprising the privacy of parties involved. All transactions and payouts can follow a publicly available smart contract, the relevant parties can see where all payments go.

Blockchain 103 serves as a reliable ledger system to attribute currencies and information to the various participants. Blockchain 103 can be decentralized, i.e., there is no entity, bank, or company that controls the blockchain and could manipulate numbers from behind the scenes. Trustworthiness is found in transparency and decentralization.

Smart contracts (i.e., executable code stored on the shared ledger of blockchain 103) can automate transactions between the data manager, medical service providers, patients and buyers of data to reach a wider market and eliminate conventional hurdles for researchers to acquire data.

As an example, the Polygon blockchain (formerly known as MATIC) can be used as blockchain 103. Polygon is a sharding-based layer-2 blockchain built on the Ethereum network. Therefore, the Polygon chain inherits Ethereum security under the SHA-256 encryption methodology. In being a layer-2 network, Polygon is able to drastically reduce fees that are typically accrued via blockchain transactions, allowing the data manager to use blockchain technology at scale with minimal fees.

Once an individual's medical record is homogenized and stored in medical data database 102, a pointer or a link to the location of the data in the database will be stored on blockchain 103 as a non-fungible token (NFT). These NFTs can be written to the ERC-721 standard, as part of a custom smart contract, such as NFT contract 112 in FIG. 1, that allows for minting (creation) of these NFTs strictly as a transparent book-keeping mechanism. The NFT can include three attributes:
- a link/pointer to the corresponding encrypted data location in medical data database 102;
- an indication of the comparable worth of this user's medical data generated by data value scoring engine 112 (in the manner described above for example); and
- the Public blockchain address of the person whose data was used.

The non-fungible tokens serve as a transparent book-keeping mechanism to identify atomic units of data, such as data records or portions of data records. The NFTs can be stored in data server wallet 106 of blockchain 103 through the (ERC-721, for example) NFT smart contract 112. Each NFTs corresponds to a data record in medial database 102, which data record points to user wallet 108b of the user that provided the data in the data record. Keep in mind that user keys are stored in secured user database 104. These database associations allow data servers 101 to identify the user/owner of anonymized data in a secure manner.

Users who provided data can get paid for the sale of their data when it is included in anonymized data sold to, for example, medical researcher 105. The sale of data from any specific user might not happen for a long time, or it might happen quickly. If users are only paid when their individual data is sold, many users might be waiting long periods of time before they would see any financial return on their data. For this reason, a smoothing model can be applied to spread out returns between the users. Based on the estimated relative value (e.g., the data score from data value scoring engine) of a user's medical data stored in medical data database 102, the user will receive "Ownership Tokens" (OWN) that represent a right to revenue from their medical data. Ownership tokens are minted by Ownership contract 114 on blockchain 103 in accordance with the determined value of the data. When any data is sold, the money received by the data manager for the sale of the data can be distributed pro-rata among all Ownership Token holders, based on a percentage of tokens owned by the user as compared to all minted ownership tokens of users who allow their medical data to be distributed. Note that, when a data record is recorded and ownership tokens are minted, some of the ownership tokens can be distributed to data server wallet 106 associated with the data manager or other wallets on blockchain 103 that are associated with other parties who have rights to a portion proceeds based on the data record.

Another advantage to the Ownership Token model is that it allows users to receive cash income from their medical data instantly by cashing out. Once a user has received their ownership tokens, they are able to sell their ownership tokens (rights to income from their data) on a secondary market. Because of Ownership Token fungibility due to this smoothing model, investors can confidently purchase income rights for anybody's medical data without viewing or receiving the private data. A free market will determine a price for Ownership Tokens at any given moment, and the data value storing engine 112 algorithm will award Ownership Tokens to users. This allows users the flexibility to cash-out their Ownership Tokens instantly in a highly liquid manner.

Periodically, for example on a yearly basis, medical data records can be updated, and any new information on the users' medical data will be added to the database record that the corresponding NFT points to, the value score of the NFT will increase, and a proportional number of Ownership Tokens will be paid out again to the user (i.e., into a user wallet corresponding to the user). While estimating the general worth of an individual's medical data is relatively straightforward, forecasting the exact worth of data is arguably impossible. The smoothing system that leverages Ownership Tokens eliminates this problem for both investors and users alike. Ownership tokens will remain fungible and receive a pro-rata payout from the data manager (data server(s) 101) sales revenue) indefinitely.

Effective medical data training sets are scarce and command high prices from researchers. Once higher quality data is available on the market en masse via system 100 of FIG. 1, the new market will create volatility. Instead of trying to anchor prices for dataset use in dollars, datasets can be priced comparatively. Datasets can be priced in another ERC-20 standard fungible token "Medical Data Market Token" (MDMT). For example, a dataset of a singular ultrasound procedure can be valued at 50 MDMT. All other data will be priced comparatively. For example, given that data of an MRI procedure is typically worth 10×what an ultrasound is worth, an MRI could cost 500 MDMT. MDMT can be made available to purchase with fiat currencies on standard crypto exchange markets. Data can still be sold in dollars, but when fiat is accepted as part of a deal for data, it will be used to purchase MDMT on the backend and then exchanged for the data. This allows for the market to set the price of medical data.

Prices can be displayed in both dollars and MDMT. MDMT will not be pegged to the dollar but will be a currency backed by its ability to purchase medical data. This makes it into a type of "stable-coin", but it is neither algorithmic nor pegged to the dollar or other fiat currency. MDMT is backed by its ability to always be exchanged for medical data, and no pricing algorithm is needed for MDMT. This reduces the possibility of any algorithmic de-pegging or crash.

Figure 2:
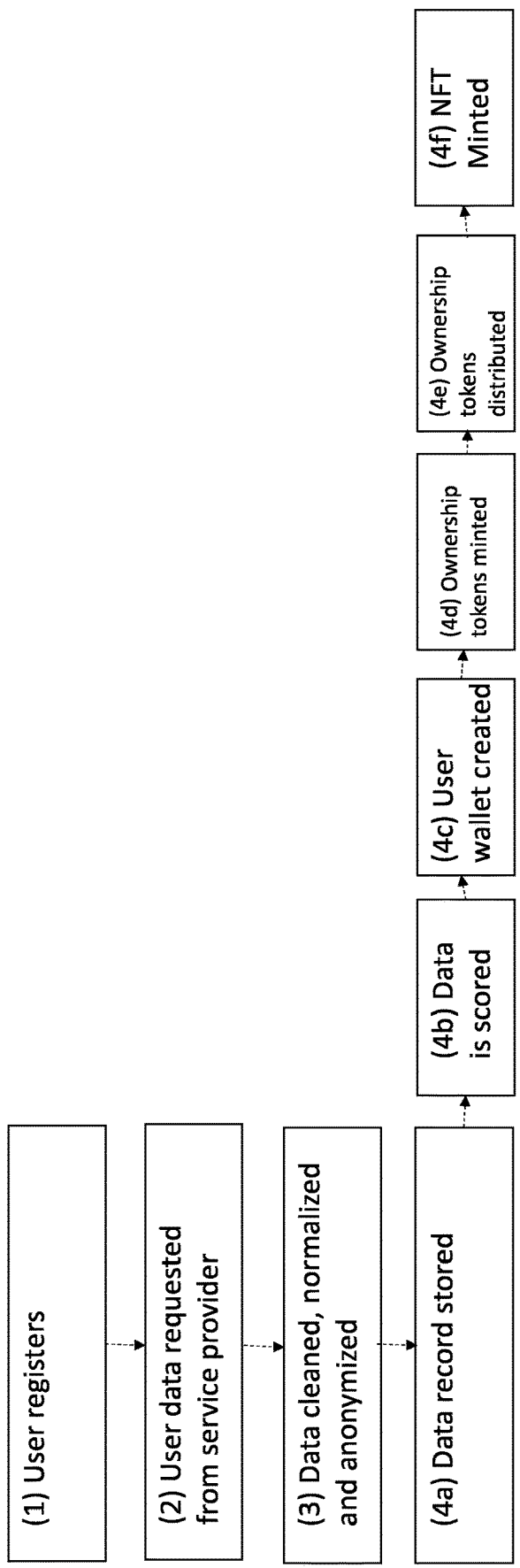
FIG. 2 is a flowchart of a data collection, management, and storage process in accordance with disclosed implementations.

FIG. 2 illustrates a method for obtaining, storing, and managing medical data in accordance with disclosed implementations. After a user registers (at 1) to allow sale of their medical data (at 2), the data manager requests the user's data from the listed medical service providers, such as provider 107. Again, the medical service provider can be a clinic, a lab or other service provider that has custody of the user's medical data. At 3, the data is transmitted to data server(s) 101, cleaned normalized and anonymized, and then stored as a data record at 4*a*. In correspondence with the data record being stored, several processes are accomplished (not necessarily in this order):

4*b*) An estimate/data-score is algorithmically generated by data pricing engine 110 of the value of the collected data;

4*c*) A user crypto wallet is automatically created on blockchain 103 for the new user (via SHA-256 encryption, for example);

4*d*) Ownership Tokens in proportion to the data-score are minted by ownership token contract 114.

4*e*) The ownership tokens are distributed to relevant wallets (for example 80 percent of the created ownership tokens can be sent to data server wallet 108*a*) and 20 percent can be sent the user crypto wallet 108*b*) in accordance with an agreed algorithm; and 4*f*) The NFT corresponding to the data record is minted by NFT contract 112, the NFT is assigned to the user wallet 108*b* and a secret key of the new user wallet is associated with the NFT, encrypted, and stored in secured user database 104.

If users are not crypto-savvy, they don't need to understand how their wallet works, and they don't even need to understand that it is a crypto wallet. Users will be able to login to their account and see a dollar value of their wallets and how much they have received. Experienced crypto users will have the option of transferring payouts and ownership tokens to their own wallet they host on a third-party platform, but the disclosed implementations can be easily used by all without requiring any crypto knowledge from users.

Figure 3:
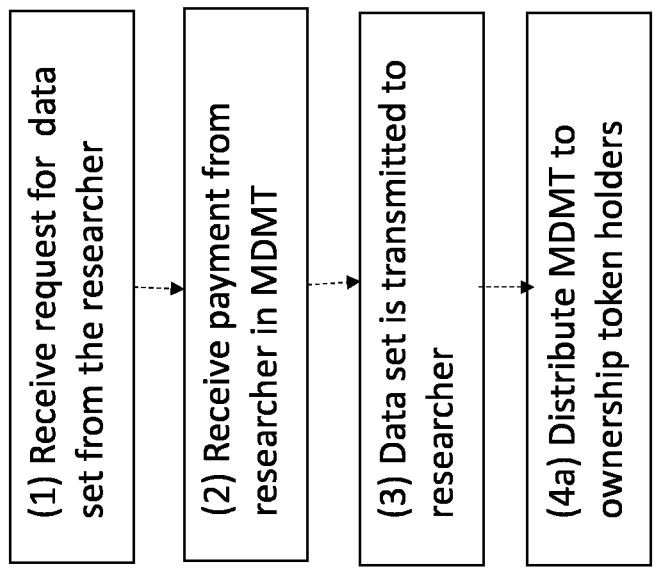
FIG. 3 is a flowchart of a data distribution process in accordance with disclosed implementations.

FIG. 3 illustrates a process for purchase/sale of data in accordance with disclosed implementations. The data records can be organized into commonly purchased datasets by data clustering engine 108. For example, one data set could be a dataset of 10,000 anonymized ultrasounds. Data sets can also be customized at the request of potential purchasers or through the use of search criteria entered through search module 106. The data sets can be priced by data pricing engine 110 in both MDMT and dollars (derived from the free-market conversion rate of MDMT). Researchers and companies that would like to purchase datasets in dollars are able to do so and as noted above, the dollars can be immediately instantly converted into MDMT. At 1, a researcher can request a data set through search module 106. At 2, the researcher can pay for the data. A MDMT smart contract 116 can be used to automate the use of the new MDMT to purchase the data on the backend through researcher wallet 104. There is no knowledge of crypto necessary for the purchase to take place. At 3, a copy of the purchased data set is transmitted to the researcher. When data is purchased, the value of MDMT that inevitably was used to purchase the data in step 3 is distributed pro-rata into the wallets of all ownership token holders.

Ownership token holders can view their rewards from their data, and the total can be displayed in both MDMT and USD. users are able to cash out their newly received MDMT in crypto, or in USD through a smart contract or connected third party that allows users to cash out their rewards. There will not be any dilution in data ownership from new Ownership tokens because ownership tokens are only minted as new data is acquired. Stated differently, every ownership token was created as new data was added, and represents value added, not dilution. Every MGMT created can be used to purchase data-sets for use in research.

The disclosed implementations provide an NFT/Crypto based system for housing medical data that allows for the development of a new Electronic Health Records system (EHR). Decentralized on the blockchain, all hospitals in the world would be able to access it given permission, and approved hospitals could update the records, ameliorating the healthcare records obstacles of both patients and providers. All sites and websites associated with the disclosed implementations can be created on a server-less build to facilitate scaling. The blockchain can be the Polygon/Matic blockchain or than any other blockchain network and protocol.

A mechanism for encrypting the data such that only certain parties can access the data can be implemented to ensure security of the system. SHA-256 keccak is the standard encryption system for much of crypto. By setting up an encryption system that adheres to SHA-256 disclosed implementations can have a master key that is used to encrypt medical data. This key will also deploy the smart contracts that manage the system. Other pieces of the blockchain will be able to verify that the key is the key that hashed a given message or signature but will be unable to replicate or reverse-engineer the cryptography. The key will then be able to authorize use of an NFT for specific addresses. This authorization can be done either on-chain or off-chain.

Data tokens can be mined by creating neural networks trained on datasets, both real and synthetic. These neural networks are then minted as new NFTs when mining is complete. Payment in data tokens can be proportional to improvement over previous versions and inversely proportional to computational cost to run algorithm for inference. Owners of data used to create these new neural networks can receive royalties from use of the neural networks.

The implementations disclosed above include both and ownership tokens and data tokens (NFT). However, various alternatives could be implemented. For example, there could be and Ownership Token only, and data can be sold in a native token, such as MATIC. Payouts could be distributed in the native token, and an oracle could set prices. Alternatively, the NFTs themselves could be owned by the user (thus also representing an ownership token), and payouts can be sent out to NFT owners in a native token. Users would be paid based on how much of their specific data gets purchased. Further, data tokens could represent both ownership of part of the data-pool, and the currency through which data is purchased. The data tokens could be used to buy data, and, by holding data tokes, user can receive payouts from data purchases.

As noted above data from multiple users can be aggregated into larger data sets with specific attributes such as longitudinal information for individual or groups of consumers, the outcome of a set of related data points, and specific data type of data regardless of any other attribute (such as aggregation of all ultrasound images). The aggregation process may place identical data into separate NFTs that have differing purposes. In such a case, the user would have compensation rights to every set containing their data. Licensees of data can either pay an upfront sum for use of the date or pay upon successful commercialization of a dataset work derivative. Users can opt in to contribution of their data in a ongoing manner. Consumers can release data for deceased persons if authorized by estate of deceased person. If a user is found to not have legal right to release data the corresponding NFT can be voided.

The NFT can be created in various ways. The NFT can be an encrypted form of the underlying data. Alternatively, the NFT can be keys and/or other necessary components to train on local encrypted NFT data. The NFT can be retained encrypted or unencrypted data where a 3rd party sends code to be trained on the data and the trained model is converted to an NFT and assigned to a 3rd party. The trained 3rd party model can be converted to the NFT which details the ownership of the model based on NFT components used to train the model. The trained 3rd party model can be run against an NFT validation set and results can be converted to the NFT for public/regulatory release of accuracy metrics. A model can be created to generate synthetic data trained on NFTs and converted to the NFT itself which is used to generate synthetic data which then becomes new training data NFT.

An outside party can use this process starting with their own data that wouldn't necessarily involve any other entity to complete. This process can include:
- encrypting their data;
- converting encrypted data into NFTs;
- converting any necessary resources necessary to work with encrypted data into NFTs;
- creating a generative model from data which is converted to NFT;
- creating other types of AI models and convert those to NFTs;
- generating synthetic data from a generative model; or converting generated synthetic data into NFTs.

Computing systems and/or logic referred to herein can comprise an integrated circuit, a microprocessor, a personal computer, a server, a distributed computing system, a communication device, a network device, or the like, and various combinations of the same. A computing system or logic may also comprise volatile and/or non-volatile memory such as random access memory (RAM), dynamic random access memory (DRAM), static random access memory (SRAM), magnetic media, optical media, nano-media, a hard drive, a compact disk, a digital versatile disc (DVD), optical circuits, and/or other devices configured for storing analog or digital information, such as in a database. A computer-readable medium, as used herein, expressly excludes paper. Computer-implemented steps of the methods noted herein can comprise a set of instructions stored on a computer-readable medium that when executed cause the computing system to perform the steps. A computing system programmed to perform particular functions pursuant to instructions from program software is a special purpose computing system for performing those particular functions. Data that is manipulated by a special purpose computing system while performing those particular functions is at least electronically saved in buffers of the computing system, physically changing the special purpose computing system from one state to the next with each change to the stored data.

The logic discussed herein may include hardware, firmware and/or software stored on a non-transient computer readable medium. This logic may be implemented in an electronic device to produce a special purpose computing system. The systems discussed herein optionally include a microprocessor configured to execute any combination of the logic discussed herein. The methods discussed herein optionally include execution of the logic by said microprocessor. The disclosed implementations are described as including various "modules", "engines", and "logic", all of which refer to executable code and a computer hardware processor for executing the code to accomplish the described functionality. The Data Storage may be distributed throughout several computing devices.

It will be appreciated by those skilled in the art that changes could be made to the implementations described above without departing from the broad inventive concept thereof. It is understood, therefore, that this invention is not limited to the particular implementations disclosed, but it is intended to cover modifications within the spirit and scope of the present invention as defined by the appended claims.

What is claimed is:

1. A method for securely collecting and storing data, the method comprising:
   receiving verification that an individual person owns data relating to the individual person;
   receiving verification that the individual person has executed a legal release, to a data manager, of the data relating to the individual person;
   sending, to a data source, by a data management system associated with the data manager, a request for the data relating to the individual person;
   in response to the request, receiving, by the data management system, the data relating to the individual person from the data source;
   storing the data relating to the individual person as a data record in a first centralized database of the data management system, whereby the data relating to the individual person is segregated in the first centralized database from other data records that correspond to other data relating to other individual persons;
   for each data record:
   dividing the record into one or more atomic units of data;
   assigning a data type to each of the one or more atomic units of data;
   creating, by a smart contract on a distributed ledger system, one or more cryptographic non-fungible tokens (NFTs), each of the one or more NFTs corresponding one of the one or more atomic units of data;
   assigning the one or more NFTs to a cryptographic wallet associated with the individual person on the distributed ledger system;
   storing a key derived from the cryptographic wallet associated with the individual person in a second centralized database;
   generating, by a smart contract on a distributed ledger system, at least one ownership token corresponding to the data record; and
   assigning a portion of the at least one ownership token to the cryptographic wallet associated with the individual person on the distributed ledger system.

2. The method of claim 1, wherein the data relating to the individual person is medical data relating to the individual person and wherein the data source is a medical service provider having custody of the medical data.

3. The method of claim 2, further comprising clustering the atomic units into data sets relevant to particular types of medical research.

4. The method of claim 1, further comprising determining a value of the each atomic unit of data and wherein the assigning a portion of an ownership token comprises assigning a portion of the ownership token based on the value of each atomic unit of data in the data record.

5. The method of claim 1, further comprising:
   receiving a search query from a party requesting data;
   retrieving relevant data from the first centralized data base that satisfies the query;
   sending the relevant data to the party requesting the data;
   receiving payment from the party requesting data; and
   distributing a portion of the payment to each individual person whose data is included in the relevant data in accordance with ownership tokens associated with the data.

6. A computer system for securely collecting and storing data, the system comprising:
- at least one computer processor; and
- at least one memory device having instructions stored therein which, when executed by the at least one computer processor cause the at least one computer processor to accomplish a method comprising:
  - receiving verification that an individual person owns data relating to the individual person;
  - receiving verification that the individual person has executed a legal release, to a data manager, of the data relating to the individual person;
- sending, to a data source, by a data management system associated with the data manager, a request for the data relating to the individual person;
  - in response to the request, receiving, by the data management system, the data relating to the individual person from the data source;
  - storing the data relating to the individual person as a data record in a first centralized database of the data management system, whereby the data relating to the individual person is segregated in the first centralized database from other data records that correspond to other data relating to other individual persons;
  - for each data record:
    - dividing the record into one or more atomic units of data;
    - assigning a data type to each of the one or more atomic units of data;
    - creating, by a smart contract on a distributed ledger system, one or more cryptographic non-fungible tokens (NFTs) each of the one or more NFTs corresponding one of the one or more atomic units of data;
    - assigning the one or more NFTs to a cryptographic wallet associated with the individual person on the distributed ledger system;
    - storing a key derived from the cryptographic wallet associated with the individual person in a second centralized database;
    - generating, by a smart contract on a distributed ledger system, at least one ownership token corresponding to the data record; and
    - assigning a portion of the at least one ownership token to the cryptographic wallet associated with the individual person on the distributed ledger system.

7. The system of claim 6, wherein the data relating to the individual person is medical data relating to the individual person and wherein the data source is a medical service provider having custody of the medical data.

8. The system of claim 7, further comprising clustering the atomic units into data sets relevant to particular types of medical research.

9. The system of claim 6, further comprising determining a value of the each atomic unit of data and wherein the assigning a portion of an ownership is based on the value of each atomic unit of data in the data record.

* * * * *